United States Patent
Geisler et al.

(10) Patent No.: US 7,067,683 B2
(45) Date of Patent: Jun. 27, 2006

(54) INDUSTRIALLY APPLICABLE PROCESS FOR THE SULFAMOYLATION OF ALCOHOLS AND PHENOLS

(75) Inventors: Jens Geisler, Berlin (DE); Frank Schneider, Schönfliess (DE); Fernando Lopez Holguin, Schmachtenhagen (DE); Kai Lovis, Berlin (DE)

(73) Assignee: Schering AG, Berlin (DE)

( * ) Notice: Subject to any disclaimer, the term of this patent is extended or adjusted under 35 U.S.C. 154(b) by 264 days.

(21) Appl. No.: 10/326,262

(22) Filed: Dec. 23, 2002

(65) Prior Publication Data

US 2003/0171346 A1 Sep. 11, 2003

Related U.S. Application Data

(60) Provisional application No. 60/341,877, filed on Dec. 21, 2001.

(51) Int. Cl.
*C07J 1/00* (2006.01)
*C07C 317/00* (2006.01)

(52) U.S. Cl. .......................................... 552/626; 568/30
(58) Field of Classification Search ................. 552/626; 568/30
See application file for complete search history.

(56) References Cited

FOREIGN PATENT DOCUMENTS

| EP | 0403185 | 12/1990 |
|---|---|---|
| WO | WO 0066095 | 11/2000 |
| WO | WO 2003/053992 A3 | 7/2003 |

OTHER PUBLICATIONS

Okada et al. "Efficient general method for sulfamoylation of a hydroxyl group.", Tetrahedron Letts., vol. 41, pp. 7047–7051, 2000.*

Schwarz et al., "Synthesis of estrogen sulfamates: Compounds with a novel endocrinological profile.", Steroids, vol. 61, pp. 710–717, 1996.*

Makoto Okada et al., "Efficient General Method for Sulfamoylation of A Hydroxyl Group," Tetrahedron Letters 41, (2000), pp. 7047–7051.

M. Okada, et al., "Efficient general method for sulphamoylation of a hyroxyl group," Tetrahedron Letters, Sep. 2000, pp. 7047–7051, vol. 41, No. 36, XP004208258, ISSN: 0040–4039 cited in the application, the whole document, Elsevier Science Publishers, Amsterdam, NL.

S. Schwarz, et al., "Synthesis of oestrogen sulphamates: compounds with a novel endocrinological profile," Steroids, Dec. 1, 1996, pp. 710–717, vol. 61, No. 12, XP004016631, ISSN: 0039–128X, p. 712, right–hand column, paragraph 2; table 3, Elsevier Science Publishers, New York, NY, US., to the extent discussed in specification.

J. Romer, et al., "Preparation and characterisation of the sulphamates of oestra–3, 17xi–diols. Rapid conversion of 16alpha–fluoro–oestradiol into 16alpha–fluoro–oestradiol–3, 17beta–disulphamate," Journal For Praktische Chemie, 1999, pp. 574–583, vol. 341, No. 6, XP002182695, ISSN: 1436–9966, cited in the application, p. 575, left–hand column, last paragraph, Wiley VCH, Weinhelm, DE., to the extent discussed in specification.

* cited by examiner

*Primary Examiner*—Barbara P. Badio
(74) *Attorney, Agent, or Firm*—Millen White Zelano & Branigan, P.C.

(57) ABSTRACT

This invention describes a safe method for the production of sulfamoyl chloride from chlorosulfonyl isocyanate and formic acid in the presence of a amide catalyst, taming the hazardous nature of this reaction by circumventing heat accumulation processes, as well as the sulfamoylation of alcohols and phenols with the resulting sulfamoyl chloride in N,N-dimethyl acetamide or N-methyl pyrrolidone thereby avoiding the formation of side-products which were inevitable with the methods of the prior art using dimethyl formamide or dichloromethane as a solvent. The current invention allows industrial scale applications and describes as an example the process of manufacture of the biologically active compound 17β-Hydroxyestra-1,3,5(10)-triene-3-yl sulfamate.

20 Claims, 1 Drawing Sheet

INDUSTRIALLY APPLICABLE PROCESS FOR THE SULFAMOYLATION OF ALCOHOLS AND PHENOLS

This application claims benefit of U.S. provisional application 60/341,877 filed on Dec. 21, 2001, which is filly incorporated by reference herein.

The invention relates to an industrially applicable process for the sulfamoylation of alcohols and phenols, and a safe industrial scale process for the production of the sulfamoylation reagent used herein.

The invention relates in particular to an industrial process for the manufacture of 17-Oxoestra-1,3,5(10)-trien-3-yl sulfamate (II), an intermediate for the synthesis of the pharmaceutically active 17β-Hydroxyestra-1,3,5(10)-trien-3-yl sulfamate (III).

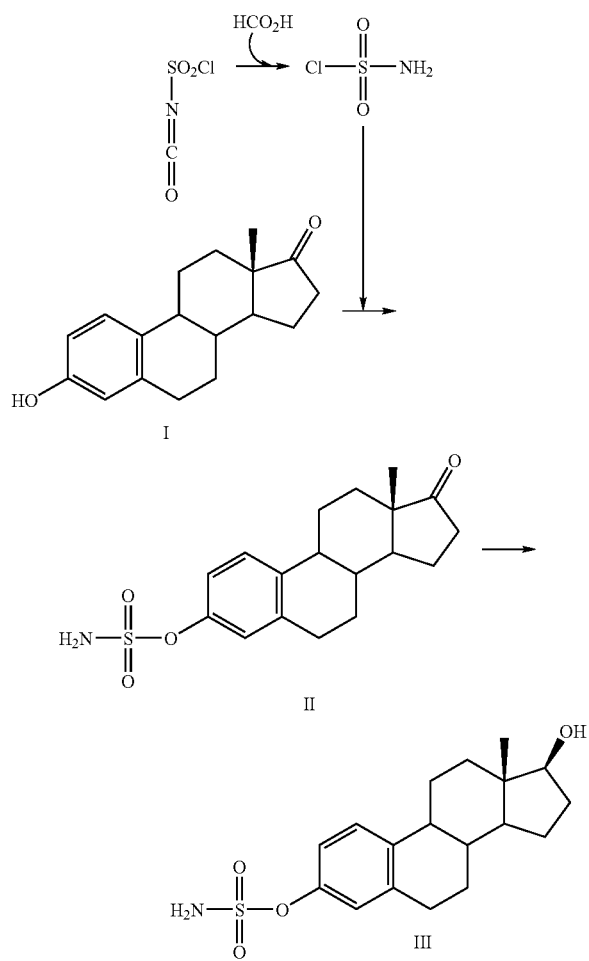

Polycyclic compounds bearing a sulfamate function, in particular steroid sulfamates have been reported to be sulfatase inhibitors. (WO93/05064).

Estra-1,3,5(10)-triene 3-yl sulfamates such as 17β-Hydroxyestra-1,3,5(10)-trien-3-yl sulfamate (WO96/05216, WO96/05217) have been described to exhibit an increased systemic and reduced hepatic estrogenicity at oral application (J. Steroid Biochem. Mol. Bio. 1995; 55, 395–403).

Sulfamates are obtained by the reaction of alcohols or phenols with sulfamoyl chloride. The known processes all apply excessive amounts of the sulfamoylating agent (sulfamoyl chloride). When dichloromethane or acetonitrile is used as solvent, additional base is required (Steroids 1999, 64, 460–471; J. Prakt. Chem 1999, 341, 574–583; J. Med. Chem. 1999, 42, 2280–2286). Nevertheless, even under these conditions the conversion rates and thus the yields are low. Due- to the high reactivity the sulfamoylating reagent tends to react with solvents. In the case of the most commonly used solvent N,N-dimethyl formamide (DMF), the formation of an undesired DMF-adduct was observed (Steroids 1996, 61, 710–717).

Sulfamoylation is the key step in the synthesis of 17β-Hydroxyestra-1,3,5(10)-trien-3-yl sulfamate, a potent estrogen after oral administration. 17-Oxo-1,3,5(10)-triene-3-ol (estrone) is reacted with sulfamoyl chloride to yield 17-Oxoestra-1,3,5(10)-trien-3-yl sulfamate, which is in turn converted to 17β-Hydroxyestra-1,3,5(10)-trien-3-yl sulfamate by means of a complex hydride reagent. According to this invention, the preferred complex hydride reagent is sodium borohydride.

Due to the problems associated, the sulfamoylation processes of the state-of-the-art did not prove suitable for a large scale industrial process for the manufacture of sulfamates, in particular for that of 17β-Hydroxyestra-1,3, 5(10)-trien-3-yl sulfamate. Sulfamoylation on a small scale is described in Tetrahedron Lett. 2000, 41, 7047–7051.

It was necessary to find an improved process for the manufacture of sulfamates from alcohols and phenols, for example from estrone, in which higher conversion rates can be reached with only a slight excess of sulfamoylating reagent and side-product formation can be reduced or avoided.

It has now been found that these problems are avoided if N,N-dimethyl acetamide (DMA) or 1-methyl-2-pyrrolidone (NMP) are used as a solvent for the sulfamoylation reaction. Moreover, by use of the solvents DMA or NMP, the amount of sulfamoyl chloride can be dramatically reduced from 5–6 equiv. in the known procedures to as low as 1.0–2 equiv. with no base present. The preferred range of the amount of sulfamoyl chloride is 1.0–1.5 equiv. Under these conditions a complete conversion to the sulfamate without formation of detectable by-products is achieved.

This procedure according to the invention has turned out to be applicable to other phenols and alcohols as well. This invention thus provides an efficient and economic method to cleanly convert a hydroxyl group to a sulfamoyloxy group using a minimum amount of the reagent in DMA or NMP.

This process allows the manufacture of sulfamates on industrial scale. Table 1 shows that the laboratory process (0.185 mol) according to this invention could successfully be scaled up to 25.5 kg (94 mol) of estrone in the pilot plant.

However, the pre-requisite for the industrial scale sulfamoylation of estrone was a safe industrial scale method for the production of sulfamoyl chloride, which is the key reagent to convert alcohols to sulfamates. This invention relates therefore to a safe production process for sulfamoyl chloride as well.

Several processes for the manufacture of sulfamoyl chloride are known. According to known processes, chlorosulfonyl isocyanate dissolved in an apriotic solvent such as an aliphatic, aromatic or chlorinated hydrocarbon, diethyl ether or acetonitrile reacts either with water (EP 0403185; Aldrichimica Acta, 10, 2, 1977, 23–28) or with formic acid (EP 0403185) to form sulfamoyl chloride. This reaction is highly exothermic and goes along with boisterous gas evolution. Attempts to scale up these laboratory methods for pilot plant production failed. In some cases, experiments on a scale as small as of 100 g showed an uncontrollable run-away behaviour with explosive gas evolution. Extensive thermal safety measurements confirmed a tendency of heat accumulation rendering the reaction of chlorosulfonyl isocyanate with formic acid on a larger scale hazardous. An uncontrolled onset of gas evolution and thereby an abrupt pressure jump would have a devastating effect on the industrial scale apparatus.

The risk of heat accumulation marked by the non-dosage-controlled gas evolution, and thereby the risk of a run-away reaction is in the given example particularly high because the reactive anhydride intermediate is formed faster (rate constant k1) than it could in the course of a consecutive reaction cascade with the loss of carbon monoxide (rate constant k2) and carbon dioxide (rate constant k3) collapse into the reaction product sulfamoyl chloride.

Proposed mechanism for the reaction of chlorosulfonyl isocyanate with formic acid to yield sulfamoyl chloride.

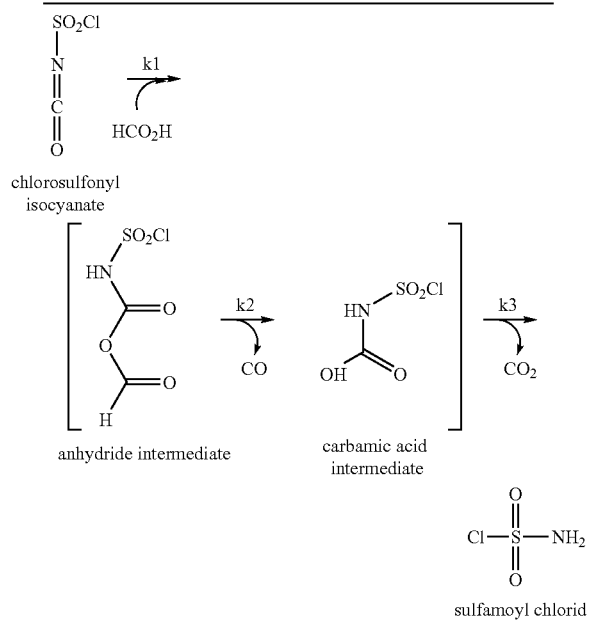

The enormous hazard potential of this process and at same time the strict safety measures made the present invention of a safe industrial method absolutely necessary. For developing an industrial scale process for the manufacture of 17β-Hydroxyestra-1,3,5(10)-trien-3-yl sulfamate, it was therefore crucial to invent a process by which the sulfamoyl chloride reagent could be provided on a large scale safely.

According to the present invention, a safe process, characterized by the dosage-controlled gas evolution is achieved by adding formic acid to a solution of chlorosulfonyl isocyanate in dichloromethane in the presence of catalytic amounts of carboxamides (typically 0.1–20 mol % relative to chlorosulfonyl isocyanate). According to the present invention, preferred catalysts include N,N-dialkyl carboxamides, more preferably N,N-dimethyl formamide or N,N-dimethyl acetamide. The preferred range of the amount of catalyst is 0.5–2 mol %. During the addition of formic acid to chlorosulfonyl isocyanate, the reaction temperature is kept in the range of 35–45°. The catalyst needn't be present in the solution of chlorosulfonyl isocyanate before formic acid is added. More preferably, the catalyst is mixed to the formic acid, which is added continuously to the reaction mixture.

Figure 1:
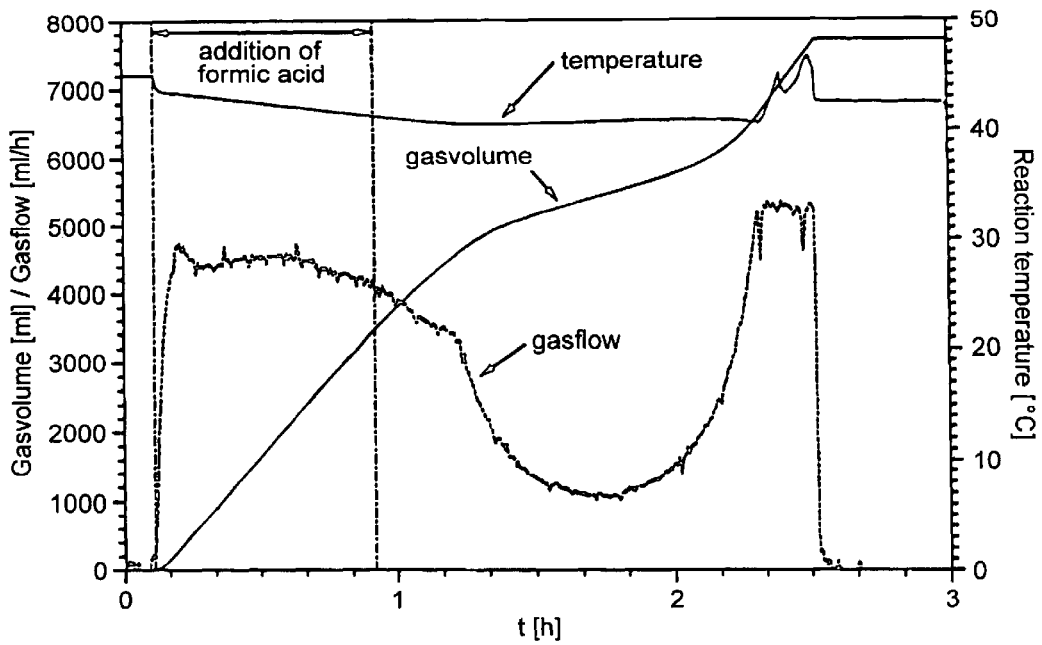
FIG. 1 depicts thermal safety measurements of the state of the art method of reaction to yield sulfamoyl chloride.
Figure 2:
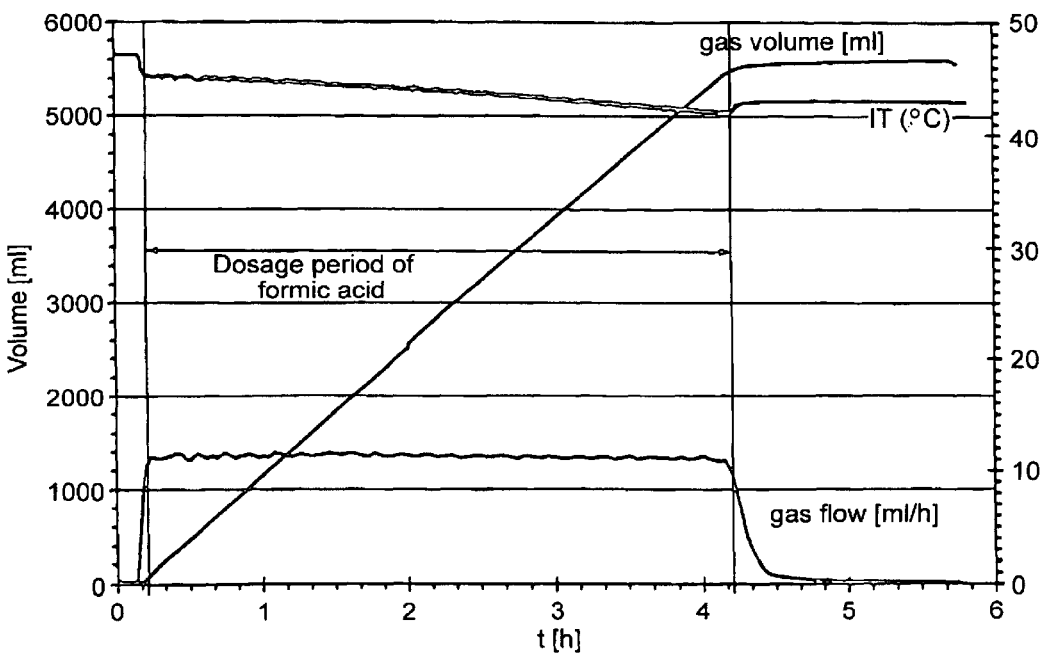
FIG. 2 depicts a thermal safety measurement in the presence of catalytic amounts of N,N-dimethyl acetamide according to an exemplary embodiment of the present invention.

The amide catalyst is thought to act by accelerating the collapse of the reactive anhydride-type intermediate into carbon monoxide and the corresponding carbamic acid, and subsequently the fragmentation thereof, resulting in carbon dioxide and sulfamoyl chloride.

Thermal safety measurements confirmed a smooth, dosage-controlled gas-flow with no indication of thermal accumulation in the presence of 0.5–2 mol %] N,N-dimethyl acetamide.

By means of the present invention, sulfamoyl chloride could safely be produced in pilot-plant batches, starting from 20 kg of chlorosulfonyl isocyanate.

TABLE 1

Synthesis of 17-Oxoestra-1,3,5(10)-trien-3-yl sulfamate (II) (according to procedure I)

| scale | yield [%] | purity* [%] |
|---|---|---|
| pilot plant (25.46 kg, 94 mol) | 93 | 98.93 |
| laboratory (50 g, 0.185 mol) | ~100 | 99.12 |

*HPLC

TABLE 2

Synthesis of 17β-Hydroxyestra-1,3,5(10)-trien-3-yl sulfamate (III) (according to procedure II)

| scale | yield [%] | purity* [%] |
|---|---|---|
| pilot plant (30.3 kg, 89.6 mol) | 80 | 99.70 |
| laboratory (60 g, 0.172 mol) | 75 | 99.61 |

*HPLC

Procedure I (Synthesis of 17-Oxoestra-1,3,5(10)-triene-3-yl Sulfamate)

A mixture of formic acid (284.92 mmol) and N,N-dimethyl acetamide (3.03 mmol) was added to a stirred solution of chlorosulfonyl isocyanate (277.47 mmol) in dichloromethane (87.5 ml) at 42° C. within a period of 3.5 hours. The mixture was heated to reflux for 15 minutes and cooled to ambient temperature. The resulting mixture was added to a stirred solution of estrone (184.93 mmol) in N,N-dimethyl acetamide (625 ml) at ambient temperature within a period of 20 minutes. The mixture was stirred at ambient temperature for 17 hours, and then poured onto water (1875 ml). After a while a white precipitate was formed. The suspension was stirred at ambient temperature for another 2 hours, and filtered. The crystals were washed twice with water (250 ml), and used without further drying and purification in the next step (Procedure II). Yield: 87.8 g (wet material) white crystals, purity (HPLC): 99.12%.

Procedure II (Synthesis of 17β-Hydroxyestra-1,3,5 (10)-trien-3-yl Sulfamate)

To a cold (2–5° C.) suspension of moist 17-Oxoestra-1,3,5(10)-trien-3-yl sulfamate (171.7 mmol, from procedure I) in ethanol (450 ml), a solution of sodium borohydride (156.23 mmol) in water (94 ml) was added at 2–5° C. within a period of 20 minutes. The resulting mixture was stirred at 2–5° C. for another 20 hours. A solution of citric acid (495.86 mmol) in water (668 ml) was then added at this temperature within a period of 15 minutes to adjust the pH to 3. Water (668 ml) was added. The resulting crystalline solid was filtered and washed three times with water (500 ml). The wet crystals were suspended in acetone (2010 ml) and the resulting suspension was heated under reflux until complete dissolution. Removal of acetone (1700 ml) by destination resulted in a suspension, which was cooled to ambient temperature and filtered. The crystalline solid was washed with cold acetone (50 ml) and dried in vacuum. Yield: 45.06 g white crystals, purity (HPLC): 99.61%.

The entire disclosure of all applications, patents and publications, cited herein and of corresponding U.S. Provisional Application Ser. No. 60/341,877, filed Dec. 21, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for producing a sulfamoyl chloride comprising reacting chlorosulfonyl isocyanate and formic acid in the presence of a carboxamide.

2. A process according to claim 1, wherein the carboxamide is present in a catalytically effective amount relative to the chlorosulfonyl isocyanate.

3. A process according to claim 2, wherein the presence of carboxamide prevents a thermal accumulation process.

4. A process according to claim 1, wherein the carboxamide is a N,N-dialkyl carboxamide.

5. A process according to claim 1, wherein the carboxamide is N,N-dimethyl formamide or N,N-dimethyl acetamide.

6. A process according to claim 5, wherein the N,N-dimethyl formamide or N,N-dimethyl acetamide is present in an amount of about 0.5—about 2 mol% relative to the chlorosulfonyl isocyanate.

7. A process for producing 17-oxoestra-1,3,5(10)-triene-3-yl sulfamate comprising:
reacting chlorosulfonyl isocyanate and formic acid in the presence of a carboxamide for producing a sulfamoyl chloride according to a process of claim 1, and
sulfamoylating estrone with the obtained sulfamoyl chloride.

8. A process for producing 17-oxoestra-1,3,5(10)-triene-3-yl sulfamate comprising:
reacting chlorosulfonyl isocyanate and formic acid in the presence of a N,N-dialkyl carboxamide for producing a sulfamoyl chloride according to a process of claim 4, and
sulfamoylating estrone with the obtained sulfamoyl chloride.

9. A process for producing 17-oxoestra-1,3,5(10)-triene-3-yl sulfamate comprising:
reacting chlorosulfonyl isocyanate and formic acid in the presence of a N,N-dimethyl formamide or N,N-dimethyl acetamide for producing a sulfamoyl chloride according to a process of claim 5, and
sulfamoylating estrone with the obtained sulfamoyl chloride.

10. A process for the production of 17β-hydroxyestra-1,3,5(10)-triene-3-yl sulfamate comprising:
reacting chlorosulfonyl isocyanate and formic acid in the presence of a carboxamide for producing a sulfamoyl chloride.
sulfamoylating estrone with the obtained sulfamoyl chloride to produce a 17-oxoestra-1,3,5(10)-triene-3-yl sulfamate according to a process of claim 7, and
reducing the obtained 17-oxoestra-1,3,5(10)-triene-3-yl sulfamate with a complex hydride reagent.

11. A process for the production of 17β-hydroxyestra-1,3,5(10)-triene-3-yl sulfamate comprising:
reacting chlorosulfonyl isocyanate and formic acid in the presence of a N,N-dialkyl carboxamide for producing a sulfamoyl chloride,
sulfamoylating estrone with the obtained sulfamoyl chloride to produce a 17-oxoestra-1,3,5(10)-triene-3-yl sulfamate according to a process of claim 8, and
reducing the obtained 17-oxoestra-1,3,5(10)-triene-3-yl sulfamate with a complex hydride reagent.

12. A process for the production of 17β-hydroxyestra-1,3,5(10)-triene-3-yl sulfamate comprising:
reacting chlorosulfonyl isocyanate and formic acid in the presence of a N,N-dimethyl formamide or N,N-dimethyl acetamide for producing a sulfamoyl chloride,
sulfamoylating estrone with the obtained sulfamoyl chloride to produce a 17-oxoestra-1,3,5(10)-triene-3-yl sulfamate according to a process of claim 9, and
reducing the obtained 17-oxoestra-1,3,5(10)-triene-3-yl sulfamate with a complex hydride reagent.

13. A process for producing sulfamates, comprising:
reacting chlorosulfonyl isocyanate and formic acid in the presence of a carboxamide for producing a sulfamoyl chloride according to a process of claim 1, and
sulfamoylating an alcohol or a phenol with the obtained sulfamoyl chloride.

14. A process for producing sulfamates, comprising:
reacting chlorosulfonyl isocyanate and formic acid in the presence of a N,N-dialkyl carboxamide for producing a sulfamoyl chloride according to a process of claim 4, and
sulfamoylating an alcohol or a phenol with the sulfamoyl chloride.

15. A process for producing sulfamates, comprising:
reacting chlorosulfonyl isocyanate and formic acid in the presence of a N,N-dimethyl formamide or N,N-dimethyl acetamide for producing a sulfamoyl chloride according to a process of claim 5, and
sulfamoylating an alcohol or a phenol with the obtained sulfamoyl chloride.

16. A process for producing sulfamates, comprising:
reacting chlorosulfonyl isocyanate and formic acid in the presence of a N,N-dimethyl formamide or N,N-dimethyl acetamide, wherein the N,N-dimethyl formamide or N,N-dimethyl acetamide is present in an amount of about 0.5—about 2 mol% relative to the chlorosulfonyl isocyanate, for producing a sulfamoyl chloride according to a process of claim 6, and
sulfamoylating an alcohol or a phenol with the obtained sulfamoyl chloride.

17. A process according to claim 1, wherein the reaction is conducted in the presence of a solvent.

18. A process according to claim 17, wherein the solvent is dichloromethane.

19. A process according to claim 1, wherein the reaction temperature is 35° C.–45° C.

20. A process according to claim 2, wherein the carboxamide is in an amount of 0.5–2 mol% relative to the chlorosulfonyl isocyanate.

* * * * *